(12) United States Patent
Librizzi

(10) Patent No.: US 8,206,821 B2
(45) Date of Patent: Jun. 26, 2012

(54) PANELS AND CONDUITS WITH ANTIMICROBIAL CHARACTERISTICS

(75) Inventor: Giuseppe Librizzi, Alabano S. Alessandro (IT)

(73) Assignee: Giuseppe Librizzi, Bergamo (IT)

( * ) Notice: Subject to any disclaimer, the term of this patent is extended or adjusted under 35 U.S.C. 154(b) by 0 days.

(21) Appl. No.: 12/090,625

(22) PCT Filed: Apr. 4, 2006

(86) PCT No.: PCT/EP2006/003033
§ 371 (c)(1), (2), (4) Date: Jul. 22, 2008

(87) PCT Pub. No.: WO2007/045284
PCT Pub. Date: Apr. 26, 2007

(65) Prior Publication Data
US 2008/0280121 A1    Nov. 13, 2008

(30) Foreign Application Priority Data

Oct. 18, 2005  (IT) .............................. MI2005A1959

(51) Int. Cl.
*B32B 3/26* (2006.01)
*B32B 27/08* (2006.01)
*B32B 27/10* (2006.01)

(52) U.S. Cl. ................ 428/319.1; 428/319.3; 428/319.7; 428/36.5; 428/36.9; 428/36.91

(58) Field of Classification Search ............... 428/319.1, 428/319.3, 319.7, 36.5, 36.9, 36.91
See application file for complete search history.

(56) References Cited

U.S. PATENT DOCUMENTS

| | | | |
|---|---|---|---|
| 3,790,520 A * | 2/1974 | Ludwig | 524/376 |
| 4,937,125 A | 6/1990 | Sanmartin et al. | |
| 5,270,108 A | 12/1993 | Savoy | |
| 5,487,412 A | 1/1996 | Mathews et al. | |
| 5,918,644 A * | 7/1999 | Haack et al. | 138/151 |
| 6,093,481 A | 7/2000 | Lynn et al. | |
| 6,579,170 B1 * | 6/2003 | Davis | 454/232 |
| 7,595,355 B2 * | 9/2009 | Trogolo | 523/122 |
| 2003/0215589 A1 | 11/2003 | Merical et al. | 428/35.7 |
| 2004/0137213 A1 * | 7/2004 | Kim | 428/323 |
| 2004/0185212 A1 | 9/2004 | Bogrett et al. | |
| 2006/0272542 A1 * | 12/2006 | Horner et al. | 106/15.05 |
| 2009/0035342 A1 * | 2/2009 | Karandikar et al. | 424/411 |

FOREIGN PATENT DOCUMENTS

| | | |
|---|---|---|
| EP | 0 940 249 A2 | 9/1999 |
| GB | 2 305 891 A | 4/1997 |
| JP | A 11-315223 | 11/1999 |
| WO | WO 2006015317 A2 * | 2/2006 |

* cited by examiner

*Primary Examiner* — Hai Vo

(57) ABSTRACT

The invention relates to the field of panels for the conveyance medium or high pressure air for ambient or to build up an ambient with air hygienically controlled, with one or more faces treated with a silver ion solution with an antimicrobial function to improve the hygiene possibilities in rooms and conduits where the panels and conduits are installed.

8 Claims, 3 Drawing Sheets

PANELS AND CONDUITS WITH ANTIMICROBIAL CHARACTERISTICS

TECHNICAL FIELD

The invention relates to panels and conduits made of polyurethane foam, in particular for the conveyance of air for environmental conditioning, with one or more faces covered with laminas of a metallic material, treated with silver ions.

BACKGROUND ART

There exist commonly known polyurethane panels and conduits with covers realized with laminas of metallic, plastic or paper material which are utilized to satisfy manifold needs whose main aim is to maintain the temperature of rooms and conduits within a pre-fixed band.

These types of polyurethane insulating panels are utilized, for example, to maintain the temperature of cold rooms.

The polyurethane insulating conduits are utilized, instead, for example, to maintain the temperature in systems for the conveyance of hot and cold air in winter and summer conditioning systems.

Some of the uses of the panels and conduits are in hospital organizations, in foodstuff production plants, in semiconductor production plants and in general in rooms where particular hygienic conditions must be respected. To maintain the necessary hygienic conditions, the panels and the conduits undergo frequent washing treatments. These treatments impose a stop to the activity or use of the rooms in which the panels and/or conduits are installed with expenditure of energy and sometimes, not succeeding, despite being washed, to reach the desired hygienic conditions. It is also known that silver ions have very potent antimicrobial properties. Likewise, it is known that silver ions are an active antimicrobial agent for at least 10 years and to obtain an antibacterial effect, the silver ions must be available in solution on the bacterial surface. The silver ions destroy bacteria instantly, blocking the enzymatic respiratory system and altering the microbial DNA and the cell wall, while they do not have toxic effects on human cells in vivo.

DISCLOSURE OF INVENTION

The aim of this invention is to realize a panel for an ambient air hygienically controlled and/or a conduit for conveyance medium or high pressure air (from 200 to 4000 Pascal) for ambient with air hygienically controlled able to perform an antimicrobial function, rendering possible a reduction in the frequency of washing treatments which are presently effected for the commonly known panels and conduits.

This aim is achieved by means of the use of silver ions applied to the surface of the panel and/or conduit covering lamina facing the interior of rooms or conduits which must respect certain hygienic conditions.

The bacteria contained in the air present inside the rooms or the conduits, upon coming into contact with the covering lamina of the panels and/or the conduits, treated with silver ions, are destroyed thanks to the antimicrobial properties of the silver ions Embodiments of the present invention include a panel comprising an insulating material made of rigid foam positioned between at least two covering sheets, characterized by the fact that silver ions are present on at least one face of at least one covering sheet. Such a covering sheet may be made of metallic material, such as aluminum, a plastic material or a paper material.

Embodiments also include a panel comprising an insulating material made of rigid foam positioned between at least two covering sheets, characterized by the fact that silver ions are present on at least one face of at least one metal covering sheet by means of a finishing varnish applied to the sheet. Embodiments also include a panel comprising an insulating material made of rigid foam positioned between two covering sheets, characterized by the fact that silver ions are present on at least one face of both metal covering sheets by means of a finishing varnish applied to the sheets (1). Embodiments also include a panel for conduits for the conveyance of air for environmental conditioning comprising an insulating material made of rigid foam positioned between at least two covering sheets, characterized by the fact that silver ions are present on at least one face of at least one covering sheet. Such embodiments may also be characterized by the fact that the covering sheet, wherever there are silver ions present, is made of metallic material, such as aluminum, a plastic material, or a paper material, and where the finishing varnish is incorporated into the covering sheet.

Embodiments also include a panel for conduits for the conveyance of air for environmental conditioning comprising an insulating material made of rigid foam positioned between at least two covering sheets, characterized by the fact that silver ions are present on at least one face of at least one metal covering sheet by means of a finishing varnish applied to the sheet, wherein the finishing varnish is incorporated into the covering sheet. Embodiments also include a panel for conduits for the conveyance of air for environmental conditioning comprising an insulating material made of rigid foam positioned between at least two covering sheets, characterized by the fact that silver ions are present on at least one face of both metal covering sheets by means of a finishing varnish applied to the sheets (1). Embodiments also include a conduit comprising an insulating material made of rigid foam positioned between at least two covering sheets, characterized by the fact that silver ions are present on at least one face of at least one covering sheet. Such embodiments may be characterized by the fact that the covering sheet, wherever there are silver ions present, is made of metallic material, such as aluminum, a plastic, or a paper material.

Embodiments also include a conduit comprising an insulating material made of rigid foam positioned between at least two covering sheets, characterized by the fact that silver ions are present on at least one side of at least one metal covering sheet by means of a finishing varnish applied to the sheet, wherein the finishing varnish is incorporated into the covering sheet. Embodiments also include a conduit comprising an insulating material made of rigid foam positioned between at least two covering sheets, characterized by the fact that silver ions are present on at least one side of both metal covering sheets by means of a finishing varnish applied to the sheets (1). Embodiments also include a conduit for the conveyance of air for environmental conditioning comprising an insulating material made of rigid foam positioned between at least two covering sheets, characterized by the fact that silver ions are present on at least one side of at least one covering sheet. Such embodiments may be characterized by the fact that the covering sheet, wherever there are silver ions present, is made of metallic material, such as aluminum, a plastic material, or a paper material.

Embodiments also include a conduit for the conveyance of air for environmental conditioning comprising an insulating material made of rigid foam positioned between at least two covering sheets, characterized by the fact that silver ions are present on at least one face of at least one covering sheet by means of a finishing varnish applied to the sheet. Embodiments also include a conduit for the conveyance of air for environmental conditioning comprising an insulating material made of rigid foam positioned between at least two covering sheets, characterized by the fact that silver ions are present on at least one face of both metal covering sheets by means of a finishing varnish applied to the sheets (1), wherein the finishing varnish is incorporated into the covering sheet.

Finally, a conduit according to any of the embodiments may be characterized by the fact that the conduit has any section.

A clearer understanding of the invention will emerge from the description that follows of a preferred embodiment, provided in the form of a non-limiting example, with reference to the accompanying drawings, in which.

Figure 1:
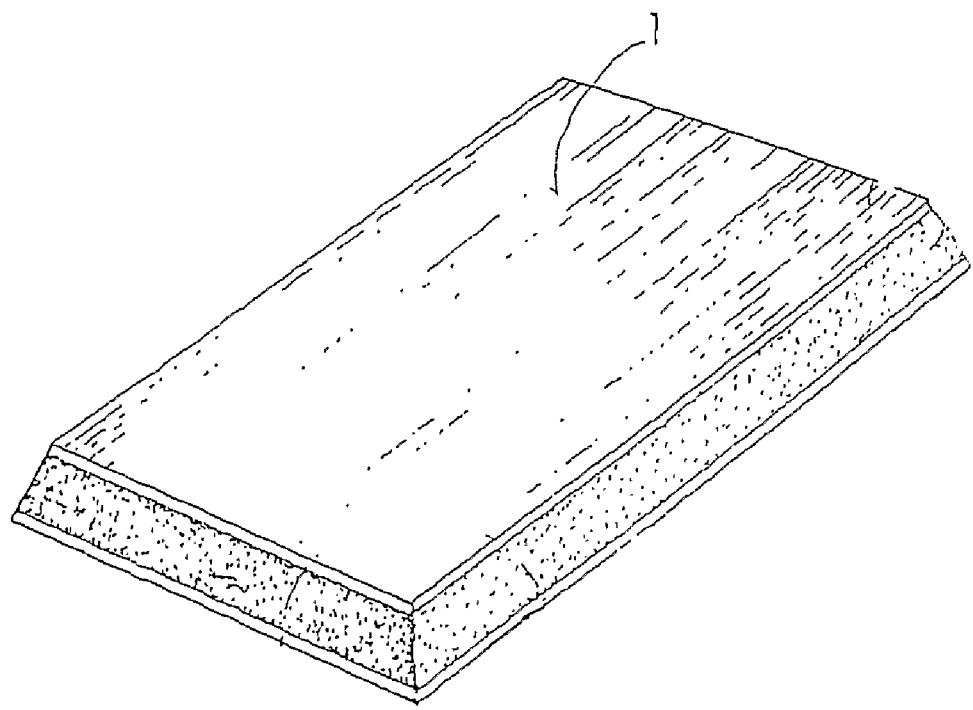
FIG. 1 shows a perspective view of the panel in question.
Figure 2:
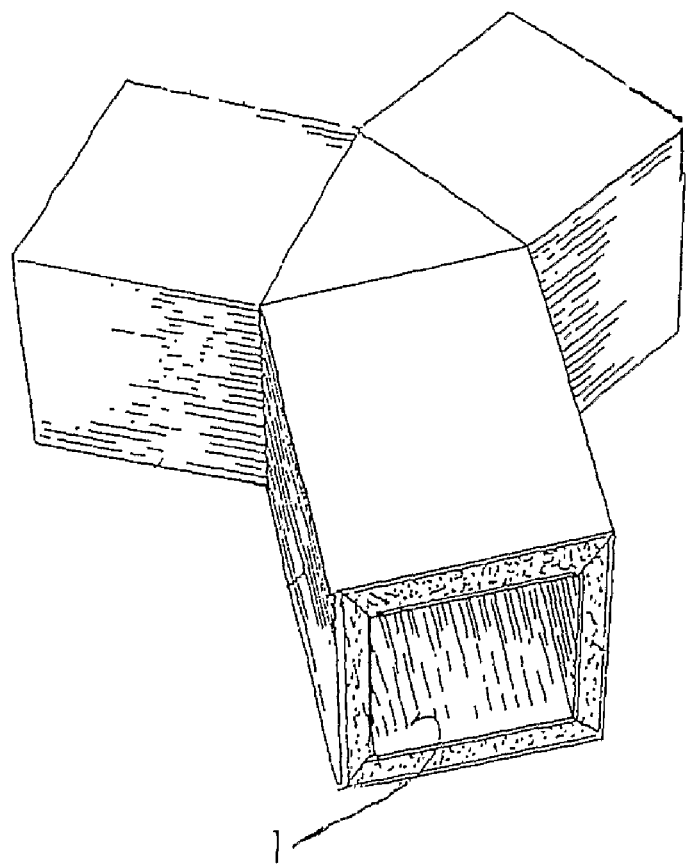
FIG. 2 shows a perspective view of a portion of the conduit realized with the panel for conduits in question.
Figure 3:
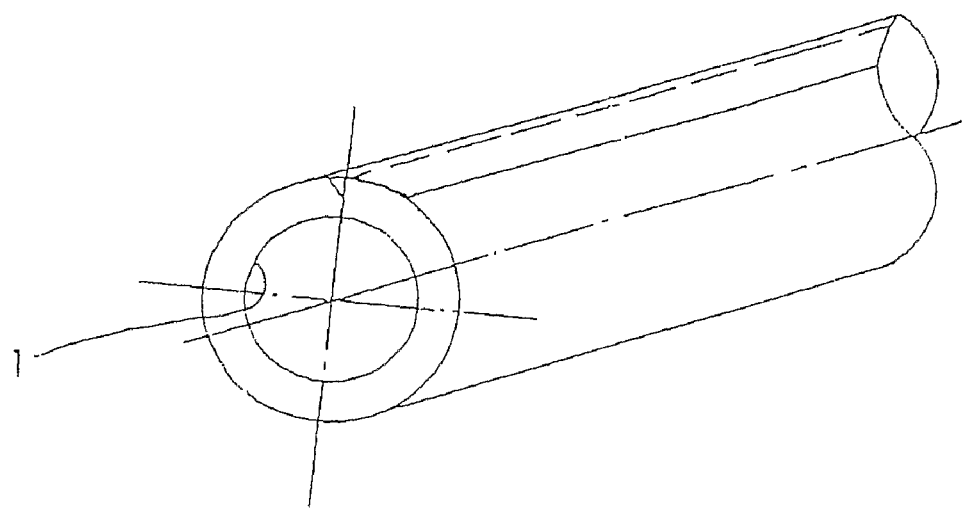
FIG. 3 shows a perspective view of a section of the conduit in question.

With reference to FIGS. 1, 2 and 3, number 1 denotes a silver ion solution and finishing varnish on the covering lamina of the panel or conduit in question spread over the entire covering surface.

The antimicrobial capacity of the silver ions occurs upon the bacteria's contact with the silver ions. Applied to the surface of the panel and/or conduit present in the room or conduit concerned is a solution in which silver ions are present. In the embodiment shown in FIGS. 1, 2 and 3, the silver ions are applied to the surface of the profiles by creating a solution of the silver ions with the finishing varnish of the covering lamina of the panel which is spread over the entire surface of the lamina.

In the description of the embodiment, specific reference is made to the application of a solution comprised of silver ions and finishing varnish to one or more covering laminas of the panel and/or conduit but naturally, the methods by which the silver ions are applied to the surface of the covering can vary according to the technical knowledge of the sector without falling beyond the scope of protection of the annexed claims.

The invention claimed is:

1. A conduit for conveying hygienically controlled air into a room, said conduit comprising at least one panel, wherein said panel includes an insulating material made of rigid foam positioned between at least two covering sheets, with one of said covering sheets facing an interior portion of said conduit, wherein said covering sheet facing said interior portion of said conduit is exposed to said hygienically controlled air passing through said conduit, and further wherein silver ions are present in said interior facing covering sheet, whereby bacteria contained in said hygienically controlled air passing through the conduit is destroyed due to antimicrobial properties of said silver ions, wherein silver ions are present by means of a finishing varnish of said interior facing covering sheet that includes a solution of said silver ions, wherein said finishing varnish is incorporated into said interior facing covering sheet, and wherein said interior facing covering sheet is in direct contact with said insulating material.

2. The conduit according to claim 1, wherein the covering sheet, where there are silver ions present, is made of metallic material.

3. The conduit according to claim 1, wherein the covering sheet, where there are silver ions present, is made of aluminum.

4. The conduit according to claim 1, wherein the covering sheet, where there are silver ions present, is made of plastic material.

5. The conduit according to claim 1, wherein the covering sheet, where there are silver ions present, is made of paper material.

6. The conduit according to claim 1, wherein said conduit is generally circular in cross-section, whereby said interior facing covering sheet is also generally circular in cross-section.

7. The conduit according to claim 1, wherein said conduit is generally rectangular in cross-section, whereby said interior facing covering sheet is also generally rectangular in cross-section.

8. The conduit according to claim 7, wherein said interior facing covering sheet is divided into four sheets.

* * * * *